United States Patent [19]

Ratkus

[11] Patent Number: 5,649,825
[45] Date of Patent: Jul. 22, 1997

[54] DENTAL ROOT CANAL BACTERIALCIDAL LUBRICANT

[76] Inventor: Victor L. Ratkus, 227 Colchester Ave., Burlington, Vt. 05401

[21] Appl. No.: 609,723

[22] Filed: Mar. 1, 1996

[51] Int. Cl.$^6$ .............. A61C 3/00; A61K 47/10; A61K 47/12; C10M 101/04
[52] U.S. Cl. .............. 433/224; 433/102; 514/789; 514/544; 514/772; 508/414
[58] Field of Search .................. 433/102, 226

[56] References Cited

U.S. PATENT DOCUMENTS

| | | | |
|---|---|---|---|
| 1,771,182 | 7/1930 | Lentulo . | |
| 1,969,808 | 8/1934 | Lentulo . | |
| 4,080,212 | 3/1978 | Takahashi | 106/35 |
| 4,260,379 | 4/1981 | Groves et al. | 433/102 |
| 4,353,698 | 10/1982 | Mespadden | 433/164 |
| 4,687,663 | 8/1987 | Schaeffer . | |
| 4,740,245 | 4/1988 | Futami et al. | 106/35 |
| 4,950,697 | 8/1990 | Chang et al. | 523/116 |
| 4,981,686 | 1/1991 | Hardy . | |
| 4,986,754 | 1/1991 | Chang et al. | 433/224 |
| 5,106,298 | 4/1992 | Heath et al. | 433/102 |
| 5,149,536 | 9/1992 | Ratkus | 424/401 |
| 5,350,298 | 9/1994 | Delaire | 433/81 |

OTHER PUBLICATIONS

EDTA and urea peroxide for root canal preparation JADA vol. 78, Feb. 1969.

*Primary Examiner*—Shep K. Rose
*Attorney, Agent, or Firm*—Charles J. Prescott

[57] ABSTRACT

An improved dental root canal bacterialcidal lubricant for allowing the cleaning wires or files to move more freely when removing a nerve from a tooth. The composition reduces packing of tissue and dentin debris within the nerve cavity. This new formulation is also resistive to decomposition during cold weather shipping and includes cetyl alcohol, stearyl alcohol, sodium lauryl sulfate, stearic acid, propylene glycol, methyl paraben, propyl paraben, butyl, paraben all in a purified (spring) water solution.

3 Claims, No Drawings

DENTAL ROOT CANAL BACTERIALCIDAL LUBRICANT

BACKGROUND OF THE INVENTION

1. Scope of Invention

This invention relates generally to endodontics and more particularly to a bacterialcidal lubricant for use in facilitating the removal of the nerve from the root canal of a tooth during endodontic therapy.

2. Prior Art

Thorough cleaning and enlarging of the root canal in conjunction with endodontic therapy has a major impact on the success of such treatment. However, due to the confined work area and the size of the equipment required for this procedure, success is not always assured.

The difficulty and importance of both removing debris and enlarging the root canal or nerve passageway, while also introducing a bacterialcidal component has been described in an article entitled "EDTA and Urea Peroxide for Root Canal Preparation" by G. Stewart in an JADA, VOL. 78, February, 1969. Summarizing this article briefly, EDTA (Disodium Ethylenediamine Tetra Acetate) was introduced in 1957 for removing calcium from both dentin and the concretions within the pulp. EDTA permits the use of reamers and files to clean and enlarge the root canal more readily and has been shown to have antimicrobial activity.

In 1961, Stewart and others introduced urea peroxide in an anhydrous glycerin base as an aid in treating infected root canals. The urea peroxide solution was stable at room temperature, while the glycerin base acted as a lubricant. Another compound, sodium hypochlorite solution reacts with hydrogen peroxide, breaking it down and liberating great quantities of oxygen. In doing so, this combination is useful in floating debris from a root canal, as well as bleaching and deodorizing the tooth. The Stewart article goes on to describe the combination of EDTA and urea peroxide as being an effective aid in cleaning and enlarging root canals. The combination also exhibited good chelating properties, helped float debris from the root canal and altered the surface of the root canal to exhibit complete penetration of medication into the tooth, Although this treatment is still now utilized in more current endodontic procedures, nonetheless it exhibits limitations of EDTA softening of tooth structure causing ledges or perforations to occur which my previous patent overcame.

My previous U.S. Pat. No. 5,149,536 provides a more effective lubricant for reducing the friction between the walls of the root canals and the file, while also providing a bacterialcidal effect. However, a problem has developed in marketing and distributing the product embodied in the claims of this '536 patent. This formulation breaks down if frozen during shipment. This original product lost most of its firmness and underwent a change in color as well, changing from a grayish off-white firm emulsion to a thin, milky-colored liquid rendering the product unusable for its intended purpose.

Applicant is also aware of U.S. Pat. No. 4,981,686 to Hardy which teaches a vaginal lubricant having some of the ingredients of the present invention, but otherwise, having nothing to do with the present invention.

BRIEF SUMMARY OF THE INVENTION

This invention is directed to an improved dental root canal bacterialcidal lubricant for allowing the cleaning wires or files to move more freely when removing a nerve from a tooth. The composition also reduces packing of tissue and dentin debris within the nerve cavity. The compound disclosed by this invention includes cetyl alcohol, stearyl alcohol, sodium lauryl sulfate, stearic acid, propylene glycol, methyl paraben, propyl paraben, butyl, paraben all in a purified (spring) water solution.

It is therefore an object of this invention to provide an improved dental root canal bacterialcidal lubricant which will not decompose when exposed to low temperatures during shipping or storage.

It is yet another object of this invention to provide a dental root canal lubricant which enhances debris removal from the root canal zone while being resistant to decomposition during temperature changes.

In accordance with these and other objects which will become apparent hereinafter, the instant invention will now be described.

DETAILED DESCRIPTION OF THE INVENTION

A dental root canal bacterialcidal lubricant in accordance with the present invention includes, in the broad sense, a long straight chain alcohol, a short chain alcohol, a long chain sulfonate salt, a low molecular weight 1, 2 diol, an alkyl para p-hydroxy benzoate and stearic acid. In a narrower sense, the preferred embodiment consists essentially of cetyl alcohol, stearyl alcohol, sodium lauryl sulfate, stearic acid, propylene glycol, methyl paraben, propyl paraben, and butyl paraben.

The following examples shown in Tables I and II herebelow are provided to illustrate both a typical preferred composition of the invention and the range of ingredients included in the invention.

TABLE I

| Ingredient | Percentage by Weight |
| --- | --- |
| Cetyl alcohol | 4.0% |
| Stearyl alcohol | 4.0% |
| Sodium lauryl sulfate | 1.0% |
| Stearic acid | 0.1% |
| Propylene glycol | 0.5% |
| Methyl paraben | 0.25% |
| Propyl paraben | 0.10% |
| Butyl paraben | 0.05% |
| Purified water | 90.0% |

TABLE II

| Ingredient | Percentage Range by Weight |
| --- | --- |
| Cetyl alcohol | 1.0% to 10.0% |
| Stearyl alcohol | 1.0% to 10.0% |
| Sodium lauryl sulfate | 0.5% to 10.0% |
| Stearic acid | 0.1% to 2.0% |
| Propylene glycol | 0.1% to 10.0% |
| Methyl paraben | 0.5% to 2.0% |
| Propyl paraben | 0.025% to 2.0% |
| Butyl paraben | 0.01% to 2.0% |
| Purified water | 52% to 96.8% |

The addition of the stearyl alcohol, a short chain alcohol, is necessary to prevent separation if the ingredients become frozen. The addition of stearic acid is required to emulsify the cetyl alcohol with the stearyl alcohol. This combination thus affords the necessary stabilization to resist decomposition during shipment in colder winter months.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A dental root canal bacterialcidal lubricant having a firm emulsion consistency which remains substantially unchanged when exposed to lower ambient temperatures by weight consisting essentially of:

A. cetyl alcohol in the range of about 1% to 10%;

B. stearyl alcohol in the range of about 1% to 10%;

C. sodium lauryl sulfate in the range of about 0.5% to 10%;

D. stearic acid in the range of about 0.1% to 2%;

E. propylene glycol in the range of about 0.1% to 10%;

F. methyl paraben in the range of about 0.5% to 2%;

G. propyl paraben in the range of about 0.025 to 2%;

H. butyl paraben in the range of about 0.01 to 2%; and

I. purified water in the range of about 52% to 97%;

said stearic acid emulsifying said cetyl alcohol and said stearyl alcohol together to substantially maintain a firm pasty consistency of said lubricant when exposed to ambient temperatures sufficiently low to freeze said lubricant.

2. In the method of removing a nerve from a root canal of a tooth during endodonic therapy with a cleaning wire or file lubricated to move more freely, wherein the improvement stable to low temperature during shipping or storage comprises removing said nerve from said tooth with a cleaning wire or file lubricated with a dental root canal bacterialcidal lubricant having a firm emulsion consistency which is resistive to decomposition when frozen, comprising:

A. cetyl alcohol;

B. stearyl alcohol;

C. sodium lauryl sulfate;

D. stearic add;

E. propylene glycol;

F. methyl paraben;

G. propyl paraben; and

H. butyl paraben;

said stearic acid acting to emulsify said cetyl alcohol together with said stearyl alcohol, said stearyl alcohol substantially resisting decomposition of said lubricant from the firm emulsion consistency to a watery consistency when said lubricant is exposed to lower ambient temperatures sufficient to cause said lubricant to substantially freeze.

3. A dental root canal bacterialcidal lubricant having a firm emulsion consistency by weight consisting essentially of:

A. cetyl alcohol in the range of about 4%;

B. stearyl alcohol in the range of about 4%;

C. sodium lauryl sulfate in the range of about 1%;

D. stearic acid in the range of about 0.1%;

E. propylene glycol in the range of about 0.5%;

F. methyl paraben in the range of about 0.25%;

G. propyl paraben in the range of about 0.1%;

H. butyl paraben in the range of about 0.05%; and

I. purified water in the range of about 90%;

said stearic acid being present to emulsify said cetyl alcohol and said stearyl alcohol together to substantially stabilize said lubricant from decomposition into a water consistency when exposed to cold winter ambient temperatures.

* * * * *